(12) United States Patent
Jacques et al.

(10) Patent No.: US 6,552,244 B1
(45) Date of Patent: Apr. 22, 2003

(54) MULTI-LAYERED WOUND DRESSING

(75) Inventors: Elizabeth Jacques, Chester (GB); Steven M. Bishop, Flintshire (GB); Michael J. Lydon, Flintshire (GB); Bryan Griffiths, Chester (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/869,909

(22) PCT Filed: Jan. 7, 2000

(86) PCT No.: PCT/EP00/00132

§ 371 (c)(1), (2), (4) Date: Oct. 5, 2001

(87) PCT Pub. No.: WO00/41661

PCT Pub. Date: Jul. 20, 2000

(30) Foreign Application Priority Data

Jan. 9, 1999 (GB) .............................................. 9900348

(51) Int. Cl.[7] .................................................. A61F 13/00
(52) U.S. Cl. ............................ 602/43; 602/41; 602/42; 602/54; 602/56
(58) Field of Search ............ 602/41–59; 424/443–449; 128/888, 889

(56) References Cited

FOREIGN PATENT DOCUMENTS

| EP | 0099748 A1 | * | 2/1984 |
| EP | 0304536 A2 | * | 3/1989 |
| EP | 0538917 A1 | * | 4/1993 |
| EP | 0849388 A1 | * | 6/1998 |
| EP | 0849388 | * | 6/1998 |

* cited by examiner

Primary Examiner—Kim M. Lewis
(74) Attorney, Agent, or Firm—John M. Kilcoyne

(57) ABSTRACT

A multi layered wound dressing comprising: (a) an adsorbent layer having high absorbency but low lateral wicking rate, and (b) a transmission layer having a high moisture vapor transmission rate overlying the side of said absorbent layer furthest from the wound.

23 Claims, 1 Drawing Sheet

MULTI-LAYERED WOUND DRESSING

CROSS-REFERENCE TO RELATED APPLICATIONS

This Application is a U.S. national phase application, filed under 35 U.S.C. §371, of International Patent Application PCT/EP00/00132, which was filed on Jan. 7, 2000; and claims priority to Great Britain Application No. 9900348, filed Jan. 9, 1999.

The present invention relates to a multi layered wound dressing particularly, but not exclusively, for use as a dressing on highly exudating wounds.

BACKGROUND OF THE INVENTION

It is known to make wound dressings for use on heavily exudating wounds from materials with a high moisture vapour transmission rate (MVTR). Such dressings rely on exudate being taken up by the dressing and spread across much of the surface area of the dressing in order to ensure sufficient moisture evaporation. Examples of such dressings are ALLEVYN marketed in adhesive or non-adhesive versions by Smith and Nephew or TIELLE marketed by Johnson and Johnson. Such dressings are not designed to absorb and retain the exudate but manage the exudate by allowing the moisture present in the exudate to evaporate. A dressing said to have a high rate of moisture evaporation is described in EP 304 536A. The dressing disclosed in this document has a flexible hydrophilic layer that absorbs exudate, sandwiched between two layers of adhesive. The absorbent layer additionally contains a fabric layer which is intended to improve the structural integrity of the dressing once it is exposed to exudate. A disadvantage of such dressings is that the lateral wicking of exudate is not contained and can cause normal skin surrounding the wound to macerate. A further disadvantage of such dressings is that the rapid loss of exudate can cause the wound to desiccate.

EP-A 0538917 discloses a vented wound dressing is disclosed comprising a thin conformable sheet material (12) at least a portion of the surface area of which it intended for placement as a dressing over a wound, which portion carries a pressure-sensitive adhesive coating (14) on one surface thereof for adhering the dressing to skin, the coating being applied to provide repeating areas (16) of the sheet material containing no adhesive, at least a portion of the repeating areas of no adhesive having slits (18) extending through the thickness thereof to permit transfer or wound fluids through the sheet material unimpeded by presence of adhesive material which can clog the slits and thereby inhibit fluid transfer therethrough.

There is thus a need for a wound dressing which is capable of absorbing exudate at the rate it is produced by a heavily exudating wound and which also does not cause maceration to the skin surrounding the wound thereby increasing the wear time of the dressing.

BRIEF SUMMARY OF THE INVENTION

We have now developed a multi layered wound dressing which alleviates the above problems and there is provided by a first embodiment of the present invention a multi layered wound dressing comprising:

(a) an absorbent layer having high absorbency but low lateral wicking;
(b) a transmission layer having a high MVTR overlying the side of said absorbent layer furthest from the wound.

We have found that wound dressings according to the invention may mitigate the problems associated with the management of high levels of exudate produced by some wounds yet not induce maceration in the skin surrounding the wound. It is thought that this is achieved by the combined use of the absorbent layer with low lateral wicking, which readily absorbs exudate and transmits it to the transmission layer.

In a second embodiment of the invention the dressing further comprises a high lateral wicking layer between the absorbent and transmission layers which aids the spread of exudate across a greater area of the dressing but away from the wound. In this way exudate is spread across a large surface area to provide sufficient moisture vapour transmission but in a location distant from the wound and skin. The passage of exudate through the dressing is therefore in a "T" shape where the lateral spread is limited in the absorbent layer and maximised in the transmission layer. Such a mechanism avoids maceration of the skin surrounding the wound since the exudate is not contained in contact with the skin. As the absorbent layer does however retain exudate in the immediate region of the wound, desiccation of the wound is avoided. This allows longer wear time for the patient and less disturbance of the wound on dressing change.

A second embodiment of the invention of the present invention provides a multi layered wound dressing comprising:

(a) an absorbent layer having high absorbency but low lateral wicking;
(b) a transmission layer having a high MVTR overlying said absorbent layer; and
(c) a spreading layer having high lateral wicking positioned between the transmission and absorbent layers, the spreading layer overlying the side of the absorbent layer furthest from the wound.

The absorbent layer is present to transport wound fluid away from the wound and absorb it while containing lateral spread of exudate. By high absorbency in the context of the present invention is meant an absorbency of at least 10 g/g preferably from 15 g/g to 50 g/g and most preferably an absorbency of from 20 g/g to 50 g/g. By low lateral wicking is meant a lateral wicking rate of less than 20 mm/60 s preferably from 1 mm/60 s to 15 mm/60 s and most preferably a lateral wicking rate of from 1 mm/60 s to 10 mm/60 s. The absorbent layer is preferably fibrous and most preferably comprises gel-forming fibres. We have found that fibrous layers as opposed to polymeric absorbent layers have the advantage that they are especially able to gel block which resists the lateral spread of exudate. In addition exudate is absorbed rapidly and retained under pressure.

The fibres suitable for use in the absorbent layer of the present invention include hydrophilic fibres, which upon the uptake of wound exudate become moist and slippery or gelatinous and thus reduce the tendency for the surrounding fibres to adhere to the wound. The fibres can be of the type, which retain their structural integrity on absorption of exudate or can be of the type, which lose their fibrous form and become a structureless gel or a solution on absorption of exudate.

The gel forming fibres are preferably spun sodium carboxymethylcellulose fibres, chemically modified cellulosic fibres, in particular carboxymethylated cellulose fibres as described in PCT WO/9312275 to Courtaulds Plc or GB93/01258 to Courtaulds Plc, pectin fibres, alginate fibres and particularly those as described in WO94/17227 to E. R. Squibb and Sons or EP 433354 to CV Laboratories Ltd or EP 476756 to CV Laboratories Ltd, or composite fibres of alginate and polysaccharide such as those described in EP 0892863 to Bristol-Myers Squibb Company, chitosan fibres, hyaluronic acid fibres, or other polysaccharide fibres or fibres derived from gums. The cellulosic fibres preferably have a degree of substitution of at least 0.05 carboxymethyl groups per glucose unit. The production of solvent-spun cellulose fibres is described for example in U.S. Pat. Nos. 4,246,221 and 4,196,281 as well as in PCT WO/9312275 mentioned above.

Preferably the gel forming fibres for use in the present invention have an absorbency of either water or saline of at least 15 g/g as measured in the free swell absorbency method, more preferably at least 25 g/g or 50 g/g. The degree of substitution of the gel forming fibre is preferably at least 0.2 carboxymethyl groups per glucose unit, more preferably between 0.3 and 0.5. The tenacity of the fibre is preferably in the range 25–15 cN/tex.

The gel forming fibres are preferably mixed to give a dressing comprising fibres of different absorbencies and also different absorbency rates and profiles. This can improve the strength and integrity of the absorbent layer in a wet or moist state.

The absorbent layer may comprise other fibres such as textile fibres which can be natural or synthetic but are preferably cellulosic fibres for example viscose rayon, multi-limbed viscose, cotton, or regenerated cellulose or fibres having a higher absorbency than most textile fibres such as the multi-limbed cellulose fibres as described in EP-A-301874. In general textile fibres absorb liquids by capillary action and are not hygroscopic this means that their absorbencies as measured by the free swell absorbency test are low such as less than 1 gram of liquid per gram of fibre.

More preferably the dressing comprises an intimate blend of gel forming fibres and cellulosic fibres in the range of 50% to 95% of textile fibres and 5% to 50% of gel forming fibres by weight. Preferably the dressing comprises a blend of fibres in the range of 65% to 80% textile fibres and 20% to 35% gel forming fibres by weight and most preferably 20% gel forming fibres and 80% textile fibres by weight.

The fibres suitable for use in the present invention can be processed using conventional textile machinery, for example by the staple route including cutting, carding and if desired crimping, drafting and spinning.

The spread layer of the present invention is preferably a net that has a high lateral wicking rate such as at least 30 mm/60 s, preferably 30 mm/60 s to 60 mm/60 s. Preferably the net is viscose polyester net such as that sold as scrim. Other nets made from composite plastic/viscose material, which are also hydrophilic, would also be suitable.

The transmission layer of the present invention is preferably a layer having a MVTR of at least 3000 g/m$^2$/24 hours measured by the method described in 1993 BP Appendix XX J1 or in the range of from 1000 g/m$^2$/24 hours to 1000 g/m$^2$/24 hours. The transmission layer may be in the form of film/foam laminate, for example expanded polyurethane foam laminated to a polyurethane film.

The dressing may also comprise additional optional layers such as an adhesive layer for adhering the dressing to the skin surrounding the wound or a soluble medicated film applied to the wound contact layer for administering a pharmaceutically active ingredient to the wound or an odour absorbing layer such as an activated carbon layer for reducing the odour from malodorous wounds. The adhesive layer may be applied to the side of dressing closest to the wound and may be provided with perforations to assist transport of exudate through the dressing. The adhesive layer may also be applied to any of the other layers to provide an island configuration.

BRIEF DESCRIPTION OF THE SEVERAL VIEWS OF THE DRAWINGS

Preferred embodiments of the present invention will now be described by way of example with reference to the accompanying drawings, in which.

DETAILED DESCRIPTION OF THE INVENTION

Figure 1:
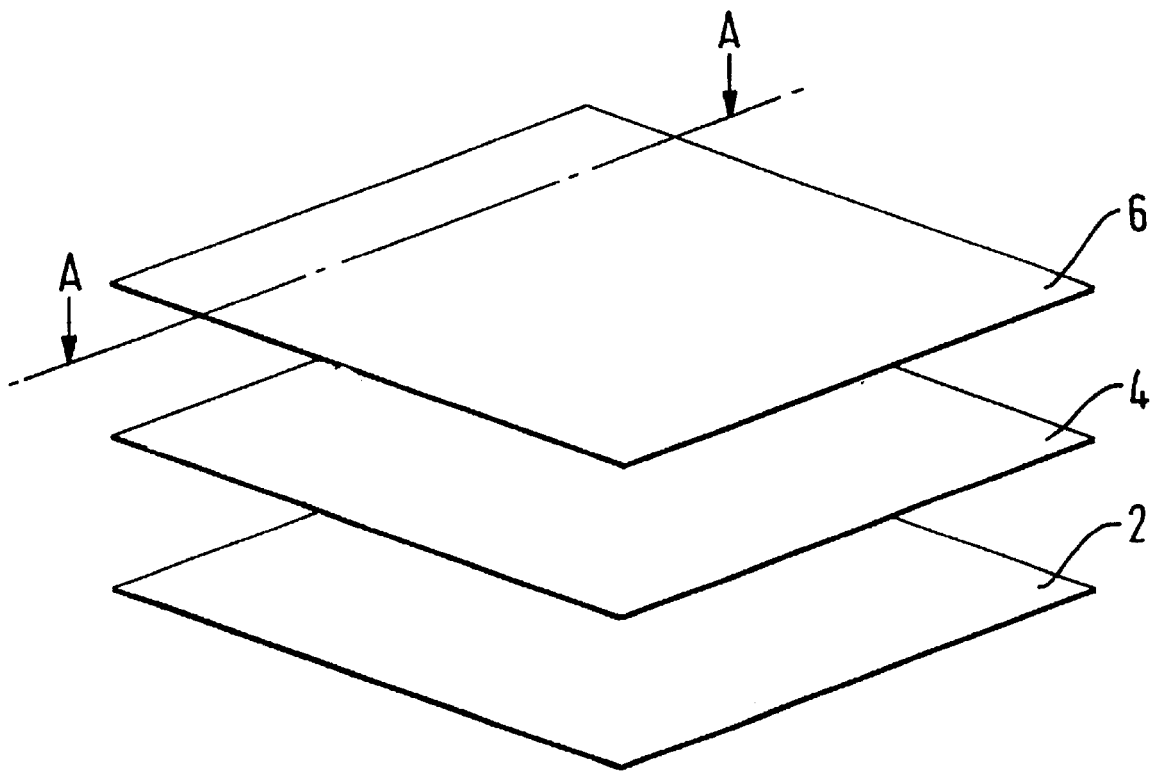
FIG. 1 is a schematic diagram of one embodiment of a multi layered wound dressing according to the invention.
Figure 2:
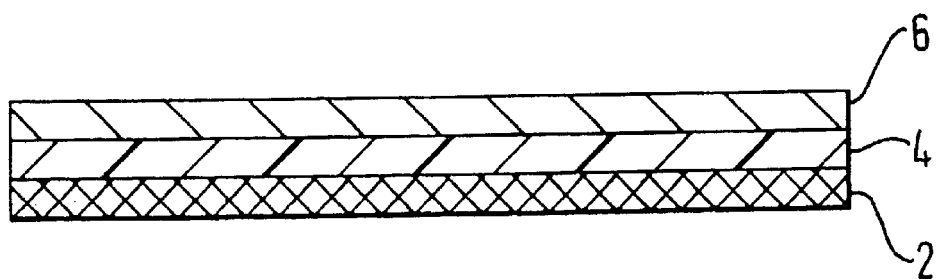
FIG. 2 shows a sectional view of the dressing of FIG. 1 taken on the line AA.

Referring now to FIG. 1 of the drawings the multi layered dressing comprises an absorbent layer (2), a spread layer (4) and a transmission layer (6). The absorbent layer is made from a 80/20 blend of cellulose fibres of the viscose rayon type with gel forming fibres such as those described in WO93/12275 to Courtaulds and sold as a fibrous dressing in the product AQUACEL ex ConvaTec. The spread layer is a net with high lateral wicking capability such as OCD ex BSF non-wovens and the transmission layer is a polyurethane foam/film laminate.

The dressing will typical y be made in three sizes, 55 mm×55 mm square, 105×15 mm square and 205×105 mm rectangular, all dressings being about 2.5 mm thick.

The dressing is placed on a wound, for example an ulcer, with the absorbent layer in contact with the wound.

Wound dressings in accordance with the present invention may reduce maceration and provide a longer wear time than known dressings.

Preferred embodiments of the invention will now be illustrated in the following examples.

EXAMPLE 1

A multi layered dressing according to the invention was made by blending the textile and gel-forming fibres in a 50/50 blend via mixing through a pre-opener and carding machine. The blended fibres were then cross-folded to the correct density, approximately 100 g/m$^2$, and needle-punched to provide appropriate tensile strength, at least 4N/cm for the final non-woven absorbent layer. The various layers as described for the embodiment of the invention shown in FIG. 1 were placed on top of one another and heat sealed together.

Optionally an adhesive was applied by extrusion in the correct dimensions onto silicone release paper and then transferred onto the absorbent layer of the dressing, either prior to or subsequent to the lamination process. In this way the adhesive is keyed into the absorbent layer via conventional pressure/heat lam-nation techniques.

The dressings were press cut or roller cut from the laminated web.

EXAMPLE 2

The MVTR of the dressing of Example 1 was measured as 750 g/m$^2$/24 hr or 1520 g/m$^2$/48 hr.

The MVTR of a dressing according to Example 1 but with an absorbent layer having an 80/20 blend of textile to gelling fibres was measured as 600 g/m$^2$/24 hr or 1410 g/m$^2$/48 hr.

MVTR was measured via the BP method referenced above.

What is claimed is:

1. A multi layered wound dressing which comprises:
   (a) an absorbent layer having a water absorbency of at least 10 g/g with a low lateral wicking rate
   (b) a transmission layer having a high moisture vapor transmission rate overlying the side of said absorbent layer furthest from the wound during use; and,
   (c) a spreading layer having high lateral wicking rate disposed between the absorbent and transmission layer.

2. The multi layered wound dressing as claimed in claim 1 wherein the passage of exudate through the wound dressing has a "T"-shaped profile.

3. The multi layered wound dressing as claimed in claim 1, wherein the absorbent layer comprises a fibrous layer.

4. The multi layered wound dressing as claimed in claim 3 wherein the fibrous layer comprises gel-forming fibres.

5. The multi layered wound dressing as claimed in claim 1, wherein the spreading layer comprises a composite plastic viscose net.

6. The multi layered wound dressing as claimed in claim 1, wherein the transmission layer comprises a foam.

7. The multi layered wound dressing as claimed in claim 1, wherein the transmission layer has a moisture vapor transmission rate of at least 1000 g/m$^2$/24 hrs.

8. The multi layered wound dressing as claimed in claim 1, further comprising an adhesive layer for adhering the multi layered wound dressing to the skin surrounding a wound.

9. The multi layered wound dressing as claimed in claim 8 wherein the adhesive layer comprises a hydrocolloid based adhesive.

10. The multi layered wound dressing as claimed in claim 1, further comprising a film layer applied to the free surface of the transmission layer.

11. A method of treating or preventing maceration of skin surrounding a wound, comprising:
   (a) providing multi layered a wound dressing comprising an absorbent layer and a transmission layer, wherein the wound dressing provides a "T" shaped profile to the passage of exudate through the wound dressing and wherein the absorbent layer exhibits a water absorbency of at least 10 g/g; and,
   (b) contacting a wound with the wound dressing.

12. A method of treating or preventing maceration of skin surrounding a wound, comprising:
   (a) providing a wound dressing comprising
      (i) an absorbent layer, wherein the absorbent layer exhibits a water absorbency of at least 10 g/g and a low lateral wicking rate;
      (ii) a transmission layer, wherein the transmission layer exhibits a high moisture vapor transmission rate; and
      (iii) a spreading layer, wherein the spreading layer exhibits a high lateral wicking and wherein the spreading layer is sandwiched between the absorbent layer and the transmission layer; and
   (b) contacting a wound with the wound dressing.

13. A multi layered wound dressing comprising:
   (a) an absorbent layer having a water absorbency of at least 10 g/g and a lateral wicking rate of less than 20 mm/60 s;
   (b) a transmission layer having a moisture vapor transmission rate of at least 1,000 g/m$^2$/24 hrs overlying the side of said absorbent layer furthest from the wound during use; and,
   (c) a spreading layer having a lateral wicking rate of at least 30 mm/60 s disposed between the absorbent layer and the transmission layer.

14. The multi layered wound dressing of claim 13, wherein the passage of exudate through the wound dressing has a "T"-shaped profile.

15. The multi layered wound dressing of claim 13, wherein the absorbent layer comprises a fibrous layer.

16. The multi layered wound dressing of claim 15, wherein the fibrous layer comprises gel-forming fibres.

17. The multi layered wound dressing of claim 13, wherein the spreading layer comprises a composite plastic viscose net.

18. The multi layered wound dressing of claim 13, wherein the transmission layer comprises a foam.

19. The multi-layered wound dressing of claim 13, wherein the transmission layer has a moisture vapor transmission rate of at least 3,000 g/m$^2$/24 hrs.

20. The multi layered wound dressing of claim 13, further comprising an adhesive layer for adhering the multi layered wound dressing to the skin surrounding the wound.

21. The multi layered wound dressing of claim 20, wherein the adhesive layer is a hydrocolloid based adhesive.

22. The multi layered wound dressing of claim 13, further comprising a film layer applied to the free surface of the transmission layer.

23. A method of treating or preventing maceration of skin surrounding a wound, comprising:
   (a) providing a wound dressing comprising
      (i) an absorbent layer having a water absorbency of at least 10 g/g and a lateral wicking rate of less than 20 mm/60 s;
      (ii) a transmission layer having a moisture vapor transmission rate of at least 1,000 g/m$^2$/24 hrs overlying the side. of said absorbent layer furthest from the wound during use; and,
      (iii) a spreading layer having a lateral wicking rate of at least 30 mm/60 s disposed between the absorbent layer and the transmission layer; and
   (b) contacting a wound with the wound dressing.

* * * * *